United States Patent
Beyer, Jr., deceased et al.

(10) Patent No.: US 6,323,203 B1
(45) Date of Patent: Nov. 27, 2001

(54) COMPOSITION AND METHOD FOR TREATING DIABETES

(75) Inventors: Karl H. Beyer, Jr., deceased, late of Gwynedd Valley, by Camille F. Beyer, legal representative; by George Q. Hardwick, legal representative, Penllyn, both of PA (US)

(73) Assignees: Camille F. Beyer, Gwynedd Valley; George Q. Hardwick, Penllyn, both of PA (US)

( * ) Notice: Subject to any disclaimer, the term of this patent is extended or adjusted under 35 U.S.C. 154(b) by 0 days.

(21) Appl. No.: 09/487,217

(22) Filed: Jan. 19, 2000

Related U.S. Application Data

(60) Provisional application No. 60/117,977, filed on Jan. 29, 1999.

(51) Int. Cl.⁷ .......................... A61K 31/50; A61K 31/495
(52) U.S. Cl. .......................... 514/247; 514/249; 514/255; 514/866
(58) Field of Search .................................... 514/247, 249, 514/255, 866

(56) References Cited

U.S. PATENT DOCUMENTS

| | | | |
|---|---|---|---|
| 4,952,582 | * | 8/1990 | Beyer, Jr. .......................... 514/255 |
| 5,110,817 | * | 5/1992 | Beyer, Jr. .......................... 514/255 |
| 5,801,177 | * | 9/1998 | Beyer, Jr. .......................... 514/255 |

* cited by examiner

*Primary Examiner*—Kevin E. Weddington
(74) *Attorney, Agent, or Firm*—Oblon, Spivak, McClelland, Maier & Neustadt, P.C.

(57) ABSTRACT

A pharmaceutical composition for treating diabetes, contains more than 600 mg of a compound of formula (I):

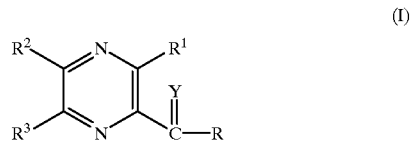

where Y is O; R is $NHCONR^4R^5$; or $N=C(NR^4R^5)_2$.
Also, another pharmaceutical composition for treating diabetes, contains a compound selected from the group consisting of compounds of formula (I):

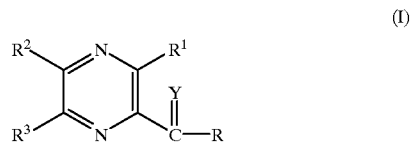

where Y is O; R is OH.

13 Claims, No Drawings

COMPOSITION AND METHOD FOR TREATING DIABETES

This application specifically references U.S. Provisional Application No. 60/117,977, filed with the U.S. Patent Office on Jan. 29, 1999.

BACKGROUND OF THE INVENTION

1. Field of the Invention

This invention relates to compositions and methods for treating diabetes.

2. Discussion of the Background

Diabetes mellitus has been defined as "a clinical syndrome characterized by a relative or inadequate deficiency of insulin or by a resistance to the action of insulin." (Ratner R E: Management of Diabetes Mellitus: Perspectives of Care Across the Lifespan. 1992, Mosby.) The definition is appropriate to the forms of diabetes that can be identified as insulin dependent diabetes mellitus (IDDM), or Type I, that requires injections of insulin to manage their loss of or insufficient pancreatic β-cell production of insulin.

Non-insulin dependent diabetes mellitus patients (NIDDM), or Type II, frequently have an increase or partial deficiency of insulin production, depending on how long the NIDDM has persisted. Regardless of the patients blood level of insulin, the hypoglycemic response to insulin is usually impaired. Patients thus exhibit postprandial and often fasting hyperglycemia, sometimes despite markedly elevated levels of insulin. Of the 13 to 15 million diabetic patients in the USA, it is estimated that up to 90% are NIDDM. By the use of surveys designed to represent their distribution, half of these NIDDM patients are undiagnosed, hence untreated. (Harris M I: Undiagnosed NIDDM: Clinical and Public Health Issues. Diabetes Care 1993;16:642–652.) Insulin production may or may not be adequate for glycemic control by proper diet and/or drug therapy.

Two determinants that influence importantly insulin resistance of cell membrane to glucose entry are: (1) availability of insulin receptors at the cell membrane, the number and activation of which is insulin-dependent, and (2) the plasma level of free fatty acids (FFA) from foodstuff and/or the lipolysis of triglyceride stores, principally in adipose tissue. Lipolysis induced by hormones, such as Norepinephrine, increases FFA blood levels available especially to muscle as a sustaining source of energy. As the blood level of FFA increases, resistance of the cell membrane to glucose uptake (insulin resistance) increases. Conversely, increased insulin blood levels as induced by the endogenous generation of hyperglycemia or by a high glucose meal (a glucose tolerance test for example) can inhibit lipolysis, and thus reduce serum FFA levels and its impedance of glucose uptake by the cells. In the non-diabetic, active person this shifting balance of a normal range of glycemia, insulin blood level and FFA lipemia makes possible exertion, sustained physical effort and consciousness over a period of hours or days between meals.

The NIDDM person is less capable of sustaining this dietary shifting balance of glycemia, insulin and FFA levels. Some may be able to approximate a normal metabolic balance if a proper diet of carbohydrate, fat and protein intake is adhered to. Exercise, a balanced life style and adjustment to or relief from stress contribute together with diet as basic therapy for these patients. Weight reduction may be an important feature of this behavior pattern since overweight and hypertension are common characteristics of NIDDM diabetes.

If this regimen of diet, exercise and adjustment to stress is insufficient to control blood sugar within appropriate limits, a sulfonylurea drug may suffice to lower blood glucose levels toward normal. These drugs are reported to stimulate insulin release from pancreatic β-cells and to increase insulin sensitivity at cell surfaces. They are usually taken just before a meal or meals. The initial (primary) response to sulfonylureas may be inadequate in 25 to 30% of patients. With time another 5 to 10% of patients develop resistance to these drugs. (Ilarde A, Tuck M: Treatment of non-insulin-dependent diabetes mellitus and its combinations. Drugs-Aging 1994;4:470–491.)

Sulfonylureas are not antihypertensive agents nor do they lower hyperlipidemic blood levels. Thus, ancillary antihypertensive and antihyperlipidemic therapy is required to diminish the high risk of cardiovascular insults such as atherosclerosis and coronary heart disease—the most frequent cause of death of these patients.

Such generally employed antihypertensive agents as thiazides and β-adrenergic blocking drugs adversely affect glucose and lipid metabolism in NIDDM persons. Most, but not all, calcium channel blocking drugs are less offensive in this regard. Angiotensin converting enzyme inhibitors do not reduce either hyperglycemia or hyperlipidemia. Their antihypertensive effect is their supportive role for these diabetic patients. Hydroxymethylglutaryl-coenzyme-A reduction inhibitors of cholesterol synthesis are relatively ineffective in lowering the frequent hyperlipidemia derived from triglyceride synthesis or lipolysis.

Nicotinic acid inhibits triglyceride hydrolysis to FFA and glycerol but is reported to be contraindicated for diabetics. (Molnar G D, Berge K G, Rosevear J W, McGuckin W F, Achor RWP: The effect of nicotinic acid in diabetes mellitus. Metabolism 1964;13;181–190.) Amiloride, a 2,4,5-tri-polar substituted pyrazinoic acid derivative, is commonly employed in formulation with a thiazide (hydrochlorothiazide) so that its potassium-retaining characteristic will offset the kaliuresis induced by the thiazide. However, amiloride or its thiazide combination should be avoided for diabetic patients because of the possibility of inducing hyperkalemia as well as hyperglycemia and hyperuricemia.

There is accordingly a need for a compound that can safely address these several needs of NIDDM patients for reduction and control of hyperglycemia, of insulin, of free fatty acid and triglyceride blood levels, and of essential (adrenergic) hypertension.

While studying pyrazinoylguanidines and their 3-amino analogs as inhibitors of urea and salt reabsorption by the kidney (i.e., as hyperuretic and saluretic agents) (Beyer K H, Gelarden R T, Vesell E S: Inhibition of urea transport across renal tubules by pyrazinoylguanidine and analogs. Pharmacology 1992;44:124–138), it was discovered that in addition to lowering urea blood levels and decreasing hypertensive blood pressure (Chambers C E, Vesell E S, Heim C, Passananti G T, Beyer K H: Pyrazinoylguanidine: Antihypertensive, hypocholesterolemic and renin effects. J. Clin. Pharmacol. 1992;32:1128–1134) these compounds and in particular the representative pyrazinoylguanidine (PZG) decreased serum concentration of triglycerides and cholesterol. (Beyer K H, Ward T D, Vary J E, Gelarden R T, Knutson D W, Vesell E S: Contrasting effects of pyrazinoylguanidine and hydrochlorothiazide in patients with renal insufficiency. J. Clin. Pharmacol. 1993;33:554–561.) Furthermore, whereas PZG had no effect on normal glucose serum concentrations, it was capable of blocking the increased serum glucose and insulin concentrations normally induced by hydrochlorothiazide in the oral glucose tolerance test (GTT). (Vesell E S, Chambers C E, Passananti G T, Demers L M, Beyer K H: Effects of pyrazinoylguanidine on the glucose-fatty acid cycle in normal subjects and patients with non-insulin-dependent diabetes mellitus. J. Clin. Pharmacol. 1993;33:823–831.) These results arose from studies of effects after 3 weeks of administration of pyrazinoylguanidine (600 mg bid po drug therapy). (Vesell et al., J. Clin. Pharmacol. 34:1234–1245, 1994; U.S. Pat. No. 5,801,177).

SUMMARY OF THE INVENTION

Accordingly, an object of this invention is to provide compositions and method of treating NIDDM persons.

Another object of the invention is to provide compositions and methods for lowering and/or controlling the blood sugar levels of NIDDM persons.

Another, object of this invention is to provide compositions and methods for lowering and/or controlling the FFA and triglyceride blood levels of NIDDM persons.

These and other objects are provided by a pharmaceutical composition, in a dosage comprising more than 600 mg of a compound of formula (I):

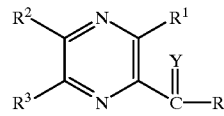

(I)

wherein Y is O;

R is NHCONR$^4$R$^5$; or N=C(NR$^4$R$^5$)$_2$;

R$^4$ and R$^5$ are each independently selected from the group consisting of hydrogen; C$_{1-10}$ alkyl, straight or branched chain, aryl C$_{1-4}$ alkyl; and mono- or disubstituted aryl C$_{1-4}$ alkyl where the substitutents are fluoro, chloro, bromo, iodo or C$_{1-10}$ alkyl, straight or branched chain;

R$^1$ and R$^2$ are each independent selected from the group consisting of hydrogen, C$_{1-10}$ alkyl, straight or branched chain, C$_{3-8}$ cycloalkyl, amino, and mono- or di-substituted amino where the substituents are C$_{1-10}$ alkyl, straight or branched chain, C$_{3-8}$ cycloalkyl; provided that R$^1$ and R$^2$ may not both be amino or substituted amino; and R$^3$ is hydrogen, trifluoromethyl, fluoro, chloro, bromo, or iodo; or a pharmaceutically acceptable salt thereof.

These compounds may be referred to collective as "the guanidines of formula (I)".

These and other objects are also achieved by administering to an NIDDM patient a composition comprising at least 600 mg of at least one of the guanidines, as a single dose.

These and other objects are also achieved by a pharmaceutical composition for treating diabetes, comprising a compound selected from the group consisting of compounds of formula (I):

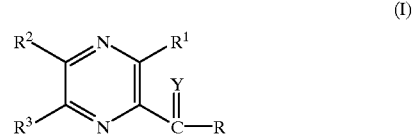

(I)

wherein Y is O;

R is OH;

R$^1$ and R$^2$ are each independent selected from the group consisting of hydrogen, C$_{1-10}$ alkyl, straight or branched chain, C$_{3-8}$ cycloalkyl, amino, and mono- or di-substituted amino where the substituents are C$_{1-10}$ alkyl, straight or branched chain, C$_{3-8}$ cycloalkyl; provided that R$^1$ and R$^2$ may not both be amino or substituted amino; and R$^3$ is hydrogen, trifluoromethyl, fluoro, chloro, bromo, or iodo; and esters, anhydrides, salts and amides thereof;

excluding the compounds where R$^1$ is amino, and R$^2$ and R$^3$ are hydrogen.

These compounds may be referred to collective as "the acids of formula (I)".

These and other objects are also achieved by administering to an NIDDM patient a composition comprising at least of the acids.

Aryl typically refers to 6 member aromatic rings, and may include other aromatic ring systems.

DETAILED DESCRIPTION OF THE PREFERRED EMBODIMENTS

In the guanidines of formula (I), preferably, R$^1$ and R$^2$ are each independent selected from the group consisting of hydrogen, amino, and mono- or di-substituted amino where the substituents are C$_{1-10}$ alkyl, straight or branched chain, C$_{3-8}$ cycloalkyl.

Most preferred compounds of the guanidines of formula (I) are those wherein for the compound of formula (I), Y is O, one of R$^1$ and R$^2$ is hydrogen; and R$^3$ is hydrogen. Particularly preferred compounds of the guanidines of formula (I) are the following: pyrazinoylguanidine (PZG) and 3-aminopyrazinoylguanidine.

In the acids of formula (I), preferably R$^1$ is selected from the group consisting of hydrogen, C$_{1-10}$ alkyl, straight or branched chain, C$_{3-8}$ cycloalkyl and mono- or di-substituted amino where the substituents are C$_{1-10}$ alkyl, straight or branched chain, C$_{3-8}$ cycloalkyl;

In the acids of formula (I), preferably R$^2$ is selected from the group consisting of hydrogen, C$_{1-10}$ alkyl, straight or branched chain, C$_{3-8}$ cycloalkyl, amino, and mono- or di-substituted amino where the substituents are C$_{1-10}$ alkyl, straight or branched chain, C$_{3-8}$ cycloalkyl;

In the acids of formula (I), more preferably R$^1$ is selected from the group consisting of hydrogen, and mono- or di-substituted amino where the substituents are C$_{1-10}$ alkyl straight or branched chain, C$_{3-8}$ cycloalkyl.

In the acids of formula (I), more preferably R$^2$ is selected from the group consisting of hydrogen, amino, and mono- or di-substituted amino where the substituents are C$_{1-10}$ alkyl straight or branched chain, C$_{3-9}$ cycloalkyl.

Most preferred compounds of the acids of formula (I) are those wherein one of R$^1$ and R$^2$ is hydrogen; and R$^3$ is hydrogen. Particularly preferred compounds of the acids of formula (I) are the following: pyrazinoic acid (PZA) and 3-aminopyrazinoic acid.

The compounds of formula (I) utilized in the present invention may be prepared in accordance with well known procedures, for example, those described in U.S. Pat. Nos. 3,313,813; 4,962,111; 5,643,912; as well as the references cited therein, all hereby incorporated by reference.

As should be noted by the structure of the preferred compounds of the present invention, the present compounds are distinguished from amiloride by the fact that those of this invention possess a low level of substitution. Amiloride is characterized by having two amino substituents, one chloro substituent and one-$CONHC(=NH)NH_2$ substituent. The multipolar amiloride-like compounds, including its 5-fluoro analog for example, share a potassium retaining hyperkalemic characteristic that has precluded general use of amiloride except in formulations to counteract the kaliuretic effect of other drugs, such as thiazides. The preferred examples of this invention are devoid of excessive retention or excretion of potassium.

It should be recognized that since these are pharmaceutical compounds it is conceivable that one of the metabolites of these compounds may be directly responsible in whole or in part for the effects observed.

The guanidines of formula (I) can be used in the form of salts derived from inorganic or organic acids. Included among such salts are the following: adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, toxylate, and undecanoate.

Combinations of the present invention may be administered orally, parenterally or rectally in dosage unit formulations containing conventional non-toxic pharmaceutically acceptable carriers, adjuvants and vehicles. The term parenteral as used herein includes subcutaneous injection, intravenous or intramuscular injection or infusion techniques. The invention is effective in the treatment of non-insulin-dependent diabetes mellitus, in the treatment of prediabetic hypertensive patients, and in the treatment of patients whose elevated glycemia, hyperlipidemia and hypertension combine as Syndrome X, risk factors for micro- or macro-cardiovascular lesions conducive to peripheral vascular and coronary artery disease.

Pharmaceutical compositions containing the active ingredient may be in a form suitable for oral use, for example, as tablets, granules, hard or soft capsules prepared according to methods known to the art for the manufacture of pharmaceutical compositions,and such compositions may contain flavoring, coloring and/or preserving agents to convey a pharmaceutically elegant and palatable preparation.

The tablets and granules may be uncoated or coated by known methods to delay disintegration and absorption in whole or in part and to delay or prolong a sustained action over a longer period of time (sustained release composition). Dispensable powders and granules suitable for preparation of an aqueous suspension for immediate oral consumption provide the active ingredient admixed with a dispersing or wetting agent, a suspending agent and one or more preservatives, coloring and/or flavoring agents. Sterile formulations for injectable solution may be prepared for packaging in dry filled form with non-toxic dispersing and solubilizing agents suitable for rapid solubilization in an aqueous solution such as normal saline for immediate injection subcutaneously, intramuscularly or intravenously. Formulations of this invention may be administered in the form of suppositories for rectal administration prepared by mixing the drug in a suitable non-irritating non-hydrous excipient which is solid at ordinary temperature but which will melt and remain fluid at rectal temperature, such as cocoa butter or polyethylene glycols. The compounds of formula (I) utilized in this invention are active on oral as well as parenteral administration.

For the acids of formula (I) dose levels of the magnitude of 10 to 2400 mg, preferably 50 to 1200 mg, more preferably 200 to 600 mg, most preferably 300 to 600 mg including all values therebetween, per day are suitably, administered once or as fractional doses twice or three times per day (eg., prior to meals). The compounds may be used alone, or in conjunction with other therapies. Acute administration is preferred, where a single dosing of the acids of formula (I) is at least 200 mg, including 200 to 1000 mg, preferably at least 300 mg, including 300 to 800 mg. Such acute administration includes a single dose of 200, 250, 300, 350, 400, 450, 500, 550, 600, 650, 700, 750, 800, 850, 900, 950 and 1000 mg. A unit dosage may be 10 to 2400 mg, but preferably is at least 200 mg, including 200 to 1000 mg, more preferably at least 300 mg, including 300 to 800 mg. Such unit dosages includes a single dosage of 200, 250, 300, 350, 400, 450, 500, 550, 600, 650, 700, 750, 800, 850, 900, 950 and 1000 mg. A unit dosage is a pill, tablet, suppository, premeasured solution, premeasured suspension, or other form of the drug specifically prepared to be taken as a single dose.

The acids of formula (I) may cause a vasomotor response similar to that of nicotinic acid. This vasomotor response, particularly in the blush area of head and neck, of variable severity and duration, is usually not hazardous. This undesirable side effect may be reduced, inhibited or eliminated, by the coadministration of prostaglandin synthesis inhibitors, for example indomethacin and aspirin, or even the guanidines of formula (I), such as PZG. Dosing levels may in an amount sufficient to inhibit prostaglandin synthesis. If a guanidine of formula (I) is use, the dosing level may be the same as the dosing levels of the guanidine of formula (I) when used alone in accordance with the invention. Preferred compositions containing the acids of formula (I) contain at least one of these prostaglandin synthesis inhibitors to inhibit the overall arachidonic-prostanoid reaction.

For the guanidines of formula (I) acute administration is preferred, where a single dosing is more than 600 mg, including more than 600 mg to 3000 mg, preferably at least 700 mg, including 700 to 2400 mg, more preferably at least 750 mg, even more preferably at least 800 mg, including 800 to 1200 mg, per day are suitably, administered once or as fractional doses twice or three times per day (eg., prior to meals). Most preferably, at least 850 mg or at least 900 mg, including 850 to 1200 mg, and 900 to 1200 mg. Such acute administration includes a single dose of 650, 700, 750, 800, 850, 900, 950, 1000, 1100, 1200, 1300, 1400, 1500, 1600, 1700, 1800, 1900, 2000, 2100, 2200, 2300 and 2400 mg. A unit dosage may be more than 600 mg to 2400 mg, but preferably is at least 700 mg, including 700 to 2400 mg, more preferably at least 750 mg, even more preferably at least 800 mg, including 800 to 1200 mg. Most preferably, a unit dosage is at least 850 mg or at least 900 mg, including 850 to 1200 mg, and 900 to 1200 mg. Such unit dosages includes a single dosage of 650, 700, 750, 800, 850, 900, 950, 1000, 1100, 1200, 1300, 1400, 1500, 1600, 1700, 1800, 1900, 2000, 2100, 2200, 2300 and 2400 mg. A unit dosage is a pill, tablet, suppository, premeasured solution, premeasured suspension, or other form of the drug specifically prepared to be taken as a single dose.

A variety of other therapies may be administered simultaneously with the guanidines of formula (I), or the acids of formula (I). Examples of these other therapies include diet therapy, as well as drugs such as Lovastatin, Glyburide, Tolbutamide, Glipizide, Verapamil, Diltiazem, Propranolol, Atenolol, Nadolol, Captopril, Enalapril and Chlorpropamide. Fully effective doses of the compounds of formula (I) may be added to or discontinued as supplement to other NIDDM therapy promptly without inducing untoward hypoglycemia, hyperglycemia or aberrant changes in measured lipids or blood pressure.

Whereas the singular features of compounds of formula (I) that relate to reduction of urea blood levels of azotemic patients, reduction of hypertensive blood pressure and hyperlipidemia have been described in previous patents (U.S. Pat. Nos. 4,594,349; 4,663,322; 4,920,123; 4,952,582; 5,110,817) and more general publications referred to therein, this invention brings to bear on a single clinical entity all these features of a single compound of formula (I) that contribute to the reduction and control of hyperglycemia and which may actually anticipate clinical NIDDM by several years as recognized on the basis of family history and clinical chemistry as pre-NIDDM patients. Genetic screening for NIDDM allows for even more precise identification of these pre-NIDDM patents. Thus, in addition to its use and safety for the control of, or as supplement to, the therapy of NIDDM, a single compound such as a preferred embodiments of examples of formula (I) can be used as preventive therapy of NIDDM, as well as its more common side effects and mortality as represented by studies of antihypertensive, antihypertriglyceridemic and antihypercholesterolemic therapy.

EXAMPLES

A three-phase study, where single oral doses of placebo, followed in one week by 900 mg of pyrazinoylguanidine (PZG), followed in three weeks by 300 mg of pyrazinoic acid (PZA), involving normal male subjects, was carried out to compare and contrast metabolic effects of single doses of PZG and PZA. A purpose of the study was to determine whether the metalbolic effects observed after 3 and also 21 days of PZG administration in patients with renal disease or with diabetes also occurred after a single oral dose.

Blood analyses preformed 0, 2 and 4 hours after administration of PZG and PZA indicated that mean values for serum glucose, insulin, C-peptide, triglycerides and free fatty acids decreased. PZG also significantly reduced very-low-density lipoprotein. Previously, it was unrecognized that acute administration of PZG and PZA could produce such rapid metabolic changes. Usually metabolic changes require subchronic or chronic administration of a compound. For example, sulfonylureas require several doses before having a metabolic effect. Administration of antithyroid compounds may require as long as two to three weeks before any metabolic effect is observed. This is also true of most antidepressant therapy.

The details of the study are described below.

Subjects

Eight male nonsmoking subjects aged 24–32 participated. They were normal by history, physical exam and routine laboratory analysis of blood and urine. They did not take any drugs chronically, nor did they consume alcoholic beverages chronically.

Study Design

This was a single-blind, three-phase crossover study beginning after a 10-hour fast at 8 a.m., designated time 0 (control), when the first venipuncture occurred. In phase I, three capsules of lactose were given orally, followed by venipunctures 2 and 4 h later. In phase II, 1 week later, after a control blood specimen drawn at 8 a.m., PZG (900 mg) was given orally and blood specimens taken 2 and 4 h thereafter. In phase III, 3 weeks later, after a control blood specimen drawn at 8 a.m., PZA (300 mg) was given orally and blood specimens taken 2 and 4 h later.

Each phase consisted of taking three capsules, each containing 300 mg. In phase I, all three capsules were of lactose; in phase II, all three were PZG; and in phase III, two capsules were lactose and one PZA. All capsules appeared indistinguishable and were given to each subject who swallowed them with water in the presence of an investigator.

The doses of PZG (900 mg) and PZA (300 mg) were selected to give comparable blood concentrations based on previous pharmacokinetic studies (Passananti et al., Pharmacology 1992:45:129–141).

Once obtained, blood specimens were immediately spun. Refrigerated serum or plasma was analyzed within 24 h for glucose, insulin, electrolytes, blood urea nitrogen, creatinine, liver function tests, triglycerides, total cholesterol, high-density lipoprotein (HDL) cholesterol, low-density lipoprotein (LDL) cholesterol, very-low-density lipoprotein (VLDL) cholesterol, free fatty acids, and fibrinogen.

Statistics

Repeated measures of analysis of variance were used to compare each subject's placebo, PZG and PZA phase. Two-tailed Student t-tests were performed between groups. All results are reported as means ±SD. Statistical significance was considered when $p<0.05$. The results are illustrated in Tables 1–4.

TABLE 1

| | PZG and PZA effects in 8 normal subjects | | | | | | | | |
|---|---|---|---|---|---|---|---|---|---|
| | Placebo phase: | | | PZG phase: | | | PZA phase: | | |
| | 0 h[1] | 2 h | 4 h | 0 h | 2 h | 4 h | 0 h | 2 h | 4 h |
| Glucose; mg/dl | | | | | | | | | |
| Mean | 84 | 84 | 85 | 87 | 84 | 80 | 84 | 85 | 80 |
| SD | 7 | 6 | 5 | 8 | 6 | 6 | 8 | 7 | 7 |
| p | — | n.s. | n.s. | — | n.s. | <0.01 | — | n.s. | n.s. |

TABLE 1-continued

PZG and PZA effects in 8 normal subjects

|  | Placebo phase: | | | PZG phase: | | | PZA phase: | | |
|---|---|---|---|---|---|---|---|---|---|
|  | 0 h[1] | 2 h | 4 h | 0 h | 2 h | 4 h | 0 h | 2 h | 4 h |
| Insulin, μU/ml | | | | | | | | | |
| Mean | 11.5 | 8.6 | 8.9 | 8.8 | 6.2 | 3.4 | 5.4 | 3.7 | 3.7 |
| SD | 4.0 | 2.0 | 1.7 | 3.0 | 1.5 | 1.2 | 3.4 | 2.5 | 1.9 |
| p | — | n.s. | n.s | — | <0.01 | <0.001 | — | <0.01 | <0.01 |
| C-peptide, ng/ml | | | | | | | | | |
| Mean | 1.0 | 0.9 | 0.9 | 1.1 | 0.9 | 0.6 | 1.2 | 1.0 | 0.7 |
| SD | 0.3 | 0.2 | 0.2 | 0.4 | 0.4 | 0.2 | 0.4 | 0.5 | 0.3 |
| p | — | n.s. | n.s. | — | 0.01 | 0.001 | — | <0.01 | <0.001 |
| Free fatty acids, meq/l | | | | | | | | | |
| Mean | 1.48 | 0.45 | 0.61 | 0.47 | 0.20 | 0.19 | 0.51 | 0.10 | 0.09 |
| SD | 0.26 | 0.22 | 0.22 | 0.15 | 0.08 | 0.05 | 0.26 | 0.06 | 0.05 |
| p | — | n.s. | <0.05 | — | <0.01 | <0.01 | — | <0.01 | <0.01 |
| Norepinephrine, pg/ml | | | | | | | | | |
| Mean | 117 | 80 | 111 | 37 | 53 | 113 | 75 | 61 | 67 |
| SD | 82 | 83 | 81 | 26 | 62 | 206 | 20 | 73 | 43 |
| p | — | n.s. | n.s. | — | n.s. | n.s. | — | n.s. | n.s. | n.s. = Not significant, $p > 0.05$.
[1]Hours correspond to immediately before PZG or PAZ (0 h), then time after drug.

TABLE 2

PZG and PZA effects in 8 normal subjects

|  | Placebo phase: | | | PZG phase: | | | PZA phase: | | |
|---|---|---|---|---|---|---|---|---|---|
|  | 0 h[1] | 2 h | 4 h | 0 h | 2 h | 4 h | 0 h | 2 h | 4 h |
| Triglycerides, mg/dl | | | | | | | | | |
| Mean | 81 | 79 | 83 | 101 | 91 | 79 | 86 | 77 | 69 |
| SD | 46 | 47 | 47 | 74 | 75 | 67 | 55 | 66 | 64 |
| p | — | n.s. | n.s. | — | <0.01 | <0.01 | — | n.s. | <0.05 |
| VLDL Cholesterol, mg/dl | | | | | | | | | |
| Mean | 16 | 16 | 17 | 20 | 18 | 16 | 17 | 15 | 14 |
| SD | 9 | 9 | 9 | 15 | 15 | 13 | 11 | 13 | 13 |
| p | — | n.s. | n.s | — | <0.01 | <0.01 | — | n.s. | n.s. |
| LDL Cholesterol, mg/dl | | | | | | | | | |
| Mean | 123 | 127 | 124 | 107 | 107 | 113 | 104 | 126 | 109 |
| SD | 33 | 32 | 32 | 26 | 28 | 26 | 35 | 40 | 37 |
| p | — | n.s. | n.s. | — | n.s. | n.s. | — | n.s. | n.s. |
| HDL Cholesterol, mg/dl | | | | | | | | | |
| Mean | 44 | 44 | 44 | 41 | 42 | 42 | 46 | 41 | 45 |
| SD | 5 | 6 | 6 | 7 | 8 | 9 | 10 | 10 | 10 |
| p | — | n.s. | n.s. | — | n.s. | n.s. | — | <0.05 | n.s. |
| Total cholesterol, mg/dl | | | | | | | | | |
| Mean | 183 | 187 | 184 | 168 | 167 | 171 | 167 | 179 | 168 |
| SD | 35 | 34 | 35 | 31 | 36 | 31 | 36 | 40 | 40 |
| p | — | n.s. | n.s. | — | n.s. | n.s. | — | <0.05 | n.s. |
| Fibrinogen, mg/dl | | | | | | | | | |
| Mean | 231 | 241 | 240 | 266 | 273 | 273 | 293 | 278 | 278 |
| SD | 32 | 36 | 43 | 46 | 56 | 49 | 73 | 67 | 64 |
| p | — | n.s. | n.s. | — | n.s. | n.s. | — | n.s. | n.s. |
| Serum concentration of PZG or PZA, μg/ml | | | | | | | | | |
| Mean | — | — | — | — | 5.1 | 3.0 | — | 5.0 | 3.0 |
| SD | — | — | — | — | 1.2 | 0.7 | — | 0.9 | 1.1 | n.s. = Not significant, $p > 0.05$.
[1]Hours correspond to immediately before PZG or PAZ (0 h), then time after drug.

TABLE 3

PZG and PZA effects in 8 normal subjects

| | Placebo phase: | | | PZG phase: | | | PZA phase: | | |
|---|---|---|---|---|---|---|---|---|---|
| | 0 h[1] | 2 h | 4 h | 0 h | 2 h | 4 h | 0 h | 2 h | 4 h |
| Renin, ng/ml per h | | | | | | | | | |
| Mean | 1.7 | 1.6 | 1.6 | 1.0 | 1.2 | 1.8 | 1.5 | 1.7 | 2.1 |
| SD | 0.7 | 0.9 | 0.9 | 0.5 | 0.6 | 0.9 | 1.1 | 0.7 | 1.3 |
| p | — | n.s. | n.s. | — | n.s. | <0.05 | — | n.s. | n.s. |
| Angiotensin I, ng/ml per h | | | | | | | | | |
| Mean | 0.81 | 0.84 | 0.92 | 0.84 | 0.86 | 1.0 | 0.66 | 0.75 | 0.73 |
| SD | 0.12 | 0.08 | 0.15 | 0.11 | 0.13 | 0.19 | 0.20 | 0.23 | 0.10 |
| p | — | n.s. | <0.001 | — | n.s. | <0.01 | — | n.s. | n.s. |
| Aldosterone, ng/dl | | | | | | | | | |
| Mean | 16.3 | 12.2 | 10.3 | 8.6 | 10.0 | 9.5 | 13.6 | 12.3 | 12.5 |
| SD | 4.5 | 3.9 | 4.2 | 3.5 | 3.6 | 2.7 | 4.7 | 4.2 | 4.9 |
| p | — | <0.05 | <0.01 | — | n.s. | n.s. | — | n.s. | n.s. |
| Potassium, meq/l | | | | | | | | | |
| Mean | 4.2 | 4.4 | 4.3 | 4.2 | 4.5 | 4.3 | 4.0 | 4.6 | 4.3 |
| SD | 0.1 | 0.3 | 0.4 | 0.1 | 0.3 | 0.2 | 0.2 | 0.4 | 0.3 |
| p | — | n.s. | n.s. | — | n.s. | n.s. | — | n.s. | n.s. |
| Urea, mg/dl | | | | | | | | | |
| Mean | 19 | 18 | 18 | 17 | 17 | 16 | 17 | 17 | 16 |
| SD | 3 | 4 | 4 | 4 | 4 | 4 | 5 | 5 | 3 |
| p | — | n.s. | n.s. | — | n.s. | n.s. | — | n.s. | n.s. |
| Uric acid, mg/dl | | | | | | | | | |
| Mean | 6.3 | 6.2 | 6.3 | 6.0 | 6.0 | 6.2 | 5.6 | 6.3 | 6.2 |
| SD | 1.4 | 1.3 | 1.3 | 0.9 | 0.9 | 0.9 | 0.9 | 1.0 | 0.9 |
| p | — | n.s. | n.s. | — | n.s. | n.s. | — | <0.01 | 0.05 | n.s. = Not significant, p >0.05.
[1] Hours correspond to immediately before PZG or PAZ (0 h), then time after drug.

Comparisons of mean serum or plasma concentrations ±SD during placebo, PZG and PZA phases are presented in Table 1 for glucose, insulin, C-peptide, free fatty acids and norepinephrine. Comparisons of mean serum or plasma concentrations ±SD during these three phases are presented in Table 2 for triglycerides, VLDL, LDL, HDL, total cholesterol, fibrinogen and serum PZG and PZA concentrations. Note the close agreement of serum PZG and PZA concentrations at 2 h and also at 4 h after their administration. Table 3 compares mean serum or plasma concentrations ±SD of renin, angiotensin I, adlosterone, potassium, urea and uric acid during the three phases of the study. As in previous studies PZG was well tolerated; no adverse reaction to PZG occurred. In an earlier pilot experiment to determine serum PZA concentrations following different PZA doses, a first subject (EV) after a single oral dose of 300 mg PZA developed unexpectedly a typical cutaneous vasomotor reaction of his blush area which included flushed, warm skin of face, neck and shoulders with a mild rash for about 90 min. After a single oral dose of 600 mg PZA, a second subject (KB) exhibited no cutaneous vasomotor reaction. Most of male volunteers exhibited cutaneous vasomotor reaction, generally like EV's. They described the reaction variously as warm redness or flushed head and neck, rash and itching (Table 4). These reactions, which were graded from 6 (most severe) to 0 (not observed), lasted from 30 min in 3 subjects to 4 h in 1 subject. One subject among the 8 had no reaction. None of the cutaneous vasomotor reactions was serious enough to interfere with participation in the study. No significant correlation occurred between score of reaction (effect+duration) and PZA peak blood concentration among the subjects (r=0.281) (Table 4).

When a reaction occurred, the onset preceded peak serum PZA concentrations, as is the case also for the cutaneous reactions associated with nicotinic acid.

TABLE 4

Cutaneous vasomotor response to a single 300-mg dose of PZA
(8 male volunteers)

| Subject | Score (0–6)[1] | PZA 2-hour serum conc, µg/ml |
|---|---|---|
| MG | 5 | 5.6 |
| RO | 4 | 3.7 |
| DM | 3 | 4.0 |
| DS | 3 | 5.4 |
| JW | 6 | 5.3 |
| MS | 2 | 5.8 |
| SB | 3 | 6.0 |
| TK | 0 | 3.9 |
| Mean | 3.25 | 4.96 |
| SD | 1.83 | 0.93 |
| r | 0.281 p > 0.05 | — |

| | | Exploratory study | | |
|---|---|---|---|---|
| | Dose | Score | Serum PZG, µg/ml | |
| Subject | Mg | (0–6) | 1 h | 2 h | t½ h |
| EV | 300 | 6 | 6.2 | 4.8 | 3 |
| KB | 600 | 0 | 10.2 | 12.0 | 5 |

[1] Score = warm + redness (flush) + rash + itching + duration. Duration as 0.5 h, 1, 2, 4 h (reaction and duration as noted).

the 4-hour duration of the comparison of PZG with PZA effects (Tables 1–3) is better suited to track some of the parameters investigated than it is for others. Generally, where PZG decreased a factor relating to the glucose-fatty-acid pathway, PZA exerted much the same effect. In this respect, PZG and PZA seem to be very similar. For example, at equivalent plasma concentrations of PZG and PZA, both reduced insulin, C-peptide, free fatty acids (Table 1) and triglyceride (Table 2) serum concentrations.

PZA has long been known to lower serum triglycerides and increase uric acid blood concentrations. (Passananti T., Vesell E, Jeszenka E, Gelarden T, Beyer K.: Pharmacokinetics of Pyrazinolyguanidine, 3-Aminopyrazinoylguanidine and Their Corresponding Pyrazinoic Acid Metabolites in Humans and Dogs, Pharmacology 1992:45:129–141; Weiner I M, Tinker J P: Pharmacology of Pyrazinamide: Metabolic and Renal Function Studies Related to the Mechanism of Drug-induced Urate Retention, J. Pharmacol. Exp. Ther. 1972:180:411–434; Ellard G A, Halsam R M: Observations on the Reduction of the Renal Elimination of Urate in Man Caused by the Administration of Pyrazinamide, Tubercle 1976:57:97–103). PZG usually does not alter plasma renin and aldosterone activity, or decreases both slightly. (Chambers C, Vesell E, Helm C, Passananti T, Beyer K: Pyrazinolyguanidine: Antihypertensive, Hypocholesterolemic, and Renin Effects, J. Clin. Pharmacol., 1992:32:1128–1134). The slight, but not significant increase in plasma renin activity in the present investigation may arise from concurrent marked elevation in plasma norepinephrine (Table 1) in response to its role to counteract inhibition of hormone-controlled lipolysis by PZG. In contrast, PZA did not elevate plasma norepinephrine (Table 1). This difference between PZG and PZA with respect to norepinephrine plasma concentration may or may not be biologically significant. In neither instance was the effect statistically significant. VLDL was decreased by both PZG and PZA, but LDL, HDL and total cholesterol were not altered systematically within this time frame (Table 2). Potassium blood concentrations were not changed by either PZG or PZA (Table 3). Uric acid plasma concentration was increased by PZA, but not by PZG (Table 3).

In this study 7 of 8 subjects responded to PZA with a cutaneous vasomotor reaction, much as occurs with nicotinic acid. This vasomotor response, particularly in the blush area of head and neck, of variable severity and duration (Table 4), while usually not hazardous, is sufficiently undesirable as to be the principal cause for lack of compliance with nicotinic acid prescribed in patient care.

In summary, the metabolic effects of PZA resemble those of nicotinic acid. Both PZA (Table 1) and nicotinic acid reduce plasma concentrations of nonesterified fatty acids and also transiently stimulate the blush area of the face, neck and shoulders. PZG shares the antilipolytic actions of PZA and nicotinic acid, but not their induction of prostaglandin $D_2$ synthesis. These two effects of nicotinic acid can be dissociated by prior administration of the prostaglandin synthesis inhibitors, indomethacin and aspirin, which abolish the vasomotor, but not the antilipolytic effect of nicotinic acid. PZG might depress the response of the body to its principal metabolite, PZA, as do indomethacin and aspirin, by inhibiting the overall arachidonic-prostanoid reaction to nicotinic acid.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for preventing the onset of symptoms of NIDDM, comprising administering to a patient in need thereof, a compound selected from the group consisting of compounds of formula (I):

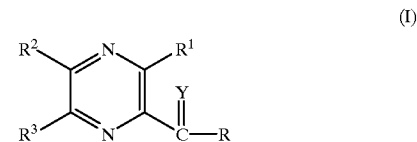

wherein Y is O;

R is $NHCONR^4R^5$; or $N=C(NR^4R^5)_2$;

$R^4$ and $R^5$ are each independently selected from the group consisting of hydrogen; $C_{1-10}$ alkyl, straight or branched chain, aryl $C_{1-4}$ alkyl; and mono- or disubstituted aryl $C_{1-4}$ alkyl where the substitutents are fluoro, chloro, bromo, iodo or $C_{1-10}$ alkyl, straight or branched chain;

$R^1$ and $R^2$ are each independent selected from the group consisting of hydrogen, $C_{1-10}$ alkyl, straight or branched chain $C_{3-8}$ cycloalkyl, amino and mono- or di-substituted amino where the substitutents are $C_{1-10}$ alkyl, straight or branched chain, $C_{3-8}$ cycloalkyl; provided that $R^1$ and $R^2$ may not both be amino or substituted amino; and $R^3$ is hydrogen, trifluoromethyl, fluoro, chloro, bromo, or iodo; or a pharmaceutically accepted salt thereof.

2. The method of claim 1 wherein said single dose is from 750 to 1200 mg of said compound.

3. The method of claim 1 wherein said single dose is at least 900 mg of said compound.

4. The method of claim 1, wherein R is $N=C(NR^4R^5)_2$.

5. The method of claim 1, wherein said compound is pyrazinoylguanidine.

6. The method of claim 1, wherein said compound is 3-aminopyrazinoylguanidine.

7. A method for preventing the onset of symptoms of NIDDM, comprising administering to a patient in need thereof, a compound selected from the group consisting of compounds of formula (I):

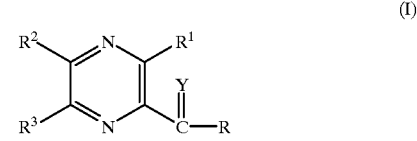

wherein Y is O;

R is OH;

$R_1$ and $R^2$ are each independent selected from the group consisting of hydrogen, $C_{1-10}$ alkyl, straight or branched chain, $C_{3-8}$ cycloalkyl, amino, and mono- or di-substituted amino where the substitutents are $C_{1-10}$ alkyl, straight or branched chain, $C_{3-8}$ cycloalkyl; provided that $R^1$ and $R^2$ may not both be amino or substituted amino; and $R^3$ is hydrogen, trifluoromethyl, fluoro, chloro, bromo, or iodo; and esters, anhydrides, salts and amides thereof;

excluding the compounds where $R^1$ is amino, and $R^2$ and $R^3$ are hydrogen.

8. The method of claim 7, wherein said single dose of 100 to 1000 mg of said compound is administered.

9. The method of claim 7, wherein a single dose of at least 300 mg of said compound is administered.

10. The method of claim 7, wherein $R^1$ is selected from the group consisting of hydrogen, and mono- or di-substituted amino where the substitutents are $C_{1-10}$ alkyl, straight or branched chain, $C_{3-8}$ cycloalkyl, $R^2$ is selected from the group consisting of hydrogen, amino, and mono- or di-substituted amino where the substituents are $C_{1-10}$ alkyl, straight or branched chain, $C_{3-8}$ cycloalkyl.

11. The method of claim 7, wherein said compound is pyrazinoic acid.

12. The method of claim 7, wherein said compound is 3-aminopyrazinoic acid.

13. The method of claim 7, further comprising administering a prostaglandin synthesis inhibitor.

* * * * *